United States Patent [19]
He

[11] Patent Number: 5,742,200
[45] Date of Patent: Apr. 21, 1998

[54] ENVIRONMENTALLY RUGGED OPTICAL SENSOR WITH IMPROVED NOISE CANCELLATION

[75] Inventor: Gang He, Morristown, N.J.

[73] Assignee: AlliedSignal Inc., Morristown, N.J.

[21] Appl. No.: 644,996

[22] Filed: May 14, 1996

[51] Int. Cl.$^6$ .............................. H03D 1/00; H03D 3/00; G01N 21/00
[52] U.S. Cl. ..................... 329/320; 329/349; 327/17; 327/63; 327/68
[58] Field of Search ..................... 329/320, 349; 327/17, 52, 63, 68; 73/23.3, 31.05, 31.06; 330/258; 356/435

[56] References Cited

U.S. PATENT DOCUMENTS 5,540,825  7/1996  Yeung et al. ................. 356/435 X

OTHER PUBLICATIONS

*AIAA 96–0303*Entitled: "Diode Laser–Based Air Mass Flux Sensor For Subsonic Aerospropulsion Inlets", by Michael F. Miller, William J. Kessler, and Mark G. Allen, Physical Sciences Inc., 34th Aerospace Sciences Meeting & Exhibit, Jan. 15–18, 1996/Reno, NV, pp. 1–10.

*Applied Optics*/vol. 34, No. 18/20 Jun. 1995, Entitled: "Ultrasensitive dual–beam absorption and gain spectroscopy: applications for near–infrared and visible diode laser sensors" pp. 3240–3249, by Mark G. Allen, Karen L. Carleton, Steven J. Davis, William J. Kessler, Charles E. Otis, Daniel A. Palombo, and David M. Sonnenfroh.

*AIAA Journal*, May, 1995, Entitled: "Simultaneous Water Vapor Concentration and Temperature Measurements Using 1.31 μm Diode Lasers", by Mark G. Allen and William J. Kessler, original pp. 1–23.

*Primary Examiner*—David Mis
*Attorney, Agent, or Firm*—Larry J. Palguta; Verne E. Kreger, Jr.

[57] ABSTRACT

A noise cancellation system which balances the photocurrents derived by a measurement signal and a reference signal of a sensor. The invention has application in any measurement device which detects a small signal in combination with high noise content and further utilizes a reference signal. The invention is useful in an optical measurement system by splitting an optical beam into measurement beam and reference optical beams; passing the measurement through a sample cell for measurement information; converting the measurement beam and reference beam into a measurement current representing information current impressed on a current signal that is modulated by undesirable noise signals and a reference current representing said carrier current signal exclusive of said information signals and modulated by said noise signals repectively; generating a voltage source as a function of said reference current and a feedback control voltage resulting in the flow of a correction current modulated by said noise signals; and combining said measurement current and said correction current in a way which substantially cancels the undesirable nosie signals from said measurement current and produces said feedback control voltage which comprises an output signal containing the information component of said measurement current. Other applications include acoustic, infared, frequency or other types of measurement systems.

3 Claims, 5 Drawing Sheets

ENVIRONMENTALLY RUGGED OPTICAL SENSOR WITH IMPROVED NOISE CANCELLATION

FIELD OF THE INVENTION

The present invention relates to optical measurement systems having circuitry for improved noise cancellation and compensation for environmental conditions.

BACKGROUND OF THE INVENTION

Several types of optical sensors have been developed for gas sensing applications, utilizing direct optical absorption techniques.

One approach to gas sensors is a broad-band IR source-based $CO_2$ sensor for space applications. In this design, a broad-band IR source illuminates a gas sample cavity and then impinges on two thermopile detectors. Optical interference narrow-band IR filters are placed in front of the two thermopile detectors. The spectral band for one of the filters is positioned within the $CO_2$ absorption band at around 4.2 µm for direct optical absorption. The spectral location of the other filter is located outside the $CO_2$ absorption band for reference purposes. The sensitivity of this device is about 1 mm Hg over a 0 to 30 mmHg $PPCO_2$ operating range. Several known problems hamper performance of this device: the sensor exhibits significant errors (up to 11%) over a 40° C. temperature range; sensor calibration depends on system operation environment, gas mixtures, and total pressure, making it less reliable for long-term applications in which these parameters may change; due to lack of self-calibration and error checking capabilities inherent in the design, the sensor calibration span is short; the sensor must be re-calibrated frequently with operator intervention; and sensor output shows significant errors due to humidity condensation in the IR absorption path during use.

The calibration dependence on gas mixture and total pressure for this device is inherent in the sensing scheme. Although narrow-band IR filters are used to provide measurement and reference signals, they are generally much wider than a number of spectral absorption lines. The line-shape for these absorption lines will be collision-broadened as the total gas pressure increases or as different gas components are added in mixture. The narrow-band pass filters may not be able to completely integrate these broadened line shapes resulting in significant integrated absorption dependence on pressure and gas mixture as well as reference band signal variations.

Device temperature dependencies may arise from several factors. One possible source is the temperature dependence of the broad-band IR source spectral output, producing an unknown temperature dependence in the ratio signal output. The thermopile detectors sense small temperature variation generated by IR energy. They are equally sensitive to small environmental temperature changes that may generate difference in both detectors. Since this sensor uses a DC sensing mode to resolve gas absorption signals, it is highly susceptible to any contamination in the optical path, since the sensor can not distinguish contamination-induced signal reduction from that of real absorption signals. These factors dictate its short operation time span and the frequent needs for system re-calibration.

Another class of gas analysis instrument consists of spectrophotometers using a broad-band source, holographic gratings, and linear CCD arrays. A typical example is a fiber-optic compact spectral analyzer marketed by Ocean Optics with typical spectral resolution range of 1 to 2 nm. Due to size limitation imposed by space application requirements, these diffraction-based devices do not offer enough resolution and sensitivity for traces of gas analysis. Due to the broadband source and low spectral resolution, these devices suffer similar problems to those of the IR $CO_2$ type sensors. In addition, the light source and instrument construction does not lend itself to a highly compact package design for space applications.

Diode laser-based spectral absorption techniques have been extensively studied and are well-documented as a reliable, high-precision, high-sensitivity, and high-specificity approach to measure gas species. Narrow-linewidth, spectral-pure (single-mode) diode lasers are wavelength-tuned to resolve an entire spectral absorption line and accurately measure absorption strength, corresponding to certain gas species. The progress of diode laser technology in the past 10 years, driven by the telecommunication, data storage, and consumer electronics industries, has led to reliable, spectrally-pure, tunable, room-temperature diode lasers operating in several optical spectral windows from 0.63 to 1.8 mm, suitable for probing a wide range of gas species. The life-time of these devices are approaching $10^4$ to $10^5$ hours, consistent with advanced space exploration applications. Semiconductor diode laser-based direct absorption sensors are most applicable for space environments since they are miniature in size, have low-power consumption, and contain no-moving parts, plumbing, gas handling, or high voltage components. They are capable of operating in high vacuum or microgavity environments. The small mechanical and thermal mass associated with diode lasers allows rapid wavelength tuning by current and temperature to scan gas spectral absorption lines, resulting in rapid sensor response speed which can satisfy a variety of monitoring, control, and warning systems requirements.

Several approaches to diode laser-based direct spectral absorption sensors have been designed. The frequency modulation spectroscopy techniques require modulating laser diodes to extremely high frequency, up to 1 Ghz, which is, in general, not practical for sensor applications from a system design perspective. The wavelength modulation spectroscopy techniques, on the other hand, modulate laser diodes with frequencies up to MHz on top of a current sweep ramp in order to overcome diode laser noises. This technique relies on phase sensitive detection to measure absorption line shapes. The reported minimum measurable absorbance is on the order $10^{-7}$, suitable for gas species trace measurements in many applications. However, the combination of phase sensitive detection, near MHz modulation, and complicated absorption signal extraction processes based on fundamental modulation frequency signal components and various harmonics make such techniques less likely to be adapted in space applications, where sensors must operate under severe environmental conditions, and multiple compensation and sensor stabilization techniques must be applied. It is apparent that it is extremely difficult to implement various system self-calibration, error-checking and compensation approaches due to the complicated system requirements. Without these required elements in place, it not likely that this type of device can satisfy space application requirements. Additionally, the complicated electronics and signal processing requirements dictate the use of very powerful microprocessors and associated elements in the final system designs, which in general lead to higher power consumption, and a less favorable device physical envelope for space applications.

U.S. Pat. No. 5,134,276 discloses a detection scheme based on a balanced ratiometric detector (BRD). A laser diode output beam is divided into measurement and reference beams. The photocurrents generated by both laser beams are electronically balanced via feedback-loop-controlled shunting of the reference beam photo-current, utilizing a super-matched transistor pair in the circuit. Using this detection scheme to cancel laser diode common-mode noises, research work demonstrated that absorbance on the level of $10^{-7}$ can be measured, when a laser diode is modulated at low frequencies (10 to 100 Hz). Such low-frequency modulation of a laser-diode output leads to a typical tuning range of 1 to 2 $cm^{-1}$ that allows full resolution of an atmospherically broadened absorption lineshape.

Certain disadvantages arising from various environmental factors must be properly addressed to fully utilize the potentials of this technology. Some disadvantages include the BRD circuit's logarithmic ratio signal which has an apparent linear temperature-dependence. This problem may be solved by temperature regulation or compensation. However, when required elements are examined for space applications, temperature regulation demands additional power that is highly limited. Furthermore, the sensor will be more susceptible to thermal shock induced errors due to the thermal recovery time and hysterisis of the regulated elements. Temperature compensation will complicate signal processing requirements and system design as each transistor pair used in the circuit may have different temperature characterisitics. If the transisor pair operating point shifted away from the linear region due to possible wide range of current loading, the temperature dependence may become nonlinear, leading to more complications in compensation schemes. Therefore, it is highly desirable that an improved BRD detection scheme be realized that takes advantage of the demonstrated high-sensitivity and simplicity of the current BRD design, while eliminating the apparent temperature sensitivity problems.

Another disadvantage is that the sensor system's self-calibration approaches for long-term applications have not been developed. Optical-based sensor response characteristics may change after initial calibrations due to factors such as laser aging, characteristics shift of optical beam splitting components, detector characteristics variations, etc. These are not unique problems for diode laser absorption gas species sensors, but common and sometimes detrimental problems for many optical based sensor systems. Practical implementation of optical-based sensors have been largely hampered by those problems, as demonstrated by their slow acceptance in applications. The successful commercial and military optical sensors to date all incorporate certain techniques to perform self-calibration functions for system stabilization. Therefore, in order for the BRD-based diode laser sensor to be successfully implemented in severe environmental condition application with long calibration span and high reliability requirements, novel self-calibration approaches must be developed to realize the potentials of this unique technology. Ideally, the self-calibration techniques to be developed are applicable to a variety of different gas species, having different sensitivity levels.

One of the major problems for direct spectral absorption diode-laser based sensors, or any other optical sensors having an open optical path, is the humidity condensation induced optical signal degradation in space life-support applications. In addition, dirt may also build up in the open optical path during long-term applications. Without an intelligent compensation approach, the possible signal amplitude degradation caused by the contamination will be interpreted as absorption signals, resulting in significant errors. Without a well developed error compensation approach, these direct absorption sensors may have short operation span and limited application range, as will similar other optical and IR sensors having an open optical path. Therefore, an intelligent error compensation approach must be developed in order to extend the BRD-based sensing approach.

From a system design point view, it is important that a BRD-based sensor design examine more closely additional issues such as overall system temperature sensitivity arising not only from sensing schemes, but also from various sensor system components such as diode lasers and detectors. For example, it is not practical to control laser diode operating temperatures with very high precision in wide operating temperature ranges. One must understand how the limited temperature-induced spectral shift of a diode-laser impacts accuracy of the sensor systems.

It is noted that the above four aspects to further improve the diode-laser BRD-based sensing scheme are generic system aspects, applicable to a variety of gas species sensors. The succesful development of these novel system self-calibration, stablization, and error compensation approaches will lead to a family of gas sensors suitable for space and other commercial applications.

SUMMARY OF THE INVENTION

The present invention is embodied as a noise cancellation system which balances the photocurrents derived by a measurement beam and a reference beam of an optical sensor.

The invention is made first by splitting an optical beam into measurement and reference optical beams; passing the measurement beam through a sample cell for measurement information; converting the meansurement beam and reference beam into a measurement current representing information signals impressed on a carrier current signal that is modulated by undersirable noise signals and a reference current representing said carrier current signal exclusive of said information signals and modulated by said noise signals repectively; generating a voltage source as a function of said reference current and a feedback control voltage, said voltage source causing the flow of a correction current modulated by said noise signals; and combining said measurement current and said correction current in a way which substantially cancels the undesirable noise signals from said measurement current and further producing said feedback control voltage which comprises an output signal containing the information component of said measurement current. The feedback control voltage contains a signal that relates to the information signals, and is separated in a digital signal processing unit.

By examining the information signals individually and comparing the signals with the original signals established at time of initial system calibration, various correction factors can be calculated to perform system self calibration. In addition, error factors such as humidity and dirt build-up induced errors, as well as system temperature sensitivity factors can also be properly compensated when the signal is at certain threshold value.

DETAILED DESCRIPTION OF THE PREFERRED EMBODIMENT OF THE INVENTION

The preferred embodiment of the invention will be illustrated as a noise suppression system for an optical sensor for use in a gas sensor in a space environment. The gas sensor application is for illustration purposes and is not intended to limit the use of the invention.

Figure 1:
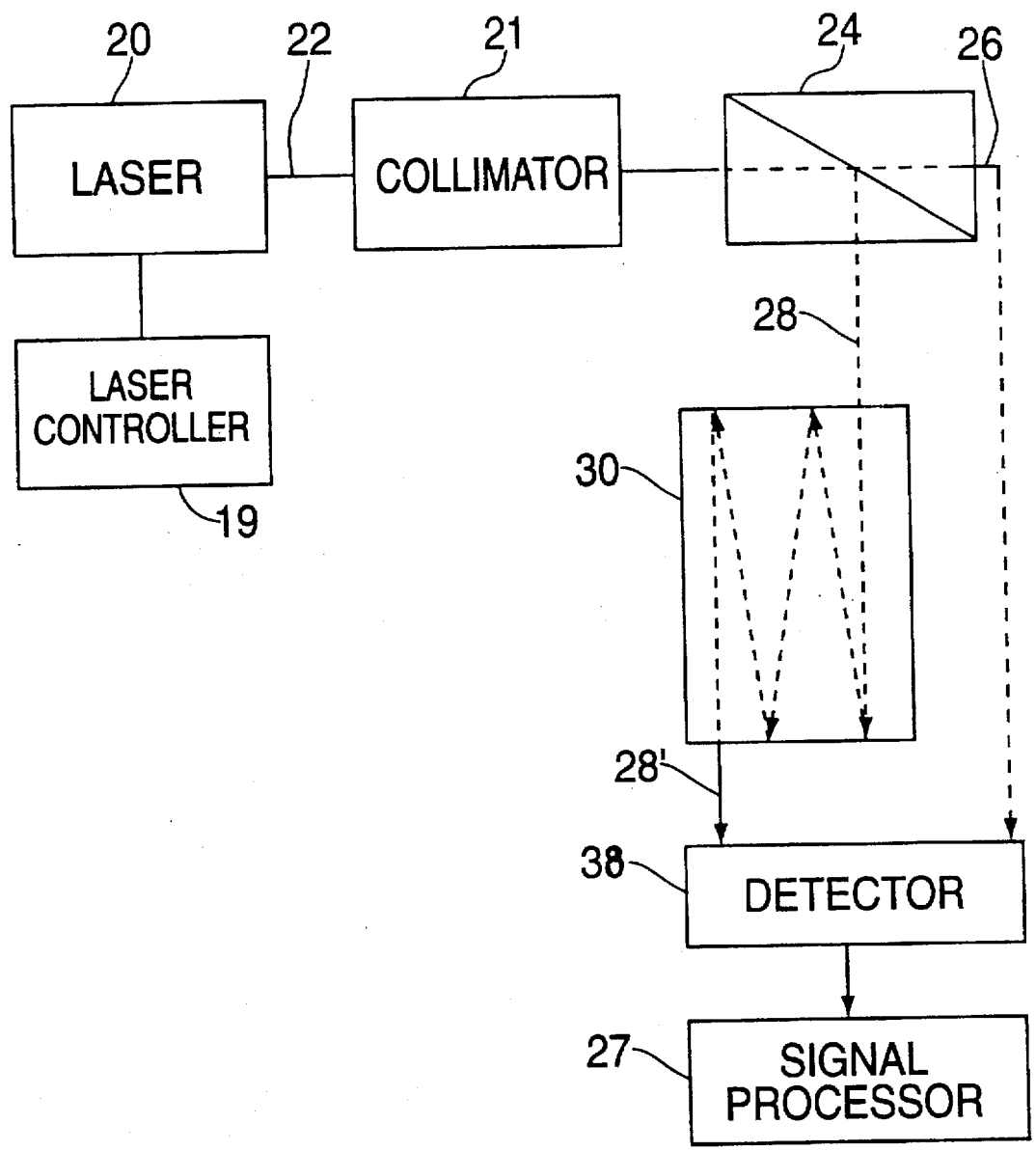
FIG. 1 is a block diagram of laser spectroscopy apparatus which is one application of the present invention.

The basic sensor system configuration is shown in FIG. 1. A controller 19 sends control signals to a Fabry-Perot (FB) or a Distributed Feedback (DFB) laser diode (0.76 μm for $O_2$ sensing, 1.57 μm for $CO_2$ sensing) 20 with proper temperature regulation. The output optical beam 22 is collimated by collimating means 21 and is divided into a reference beam 26 and a measurement beam 28 by a non-polarizing beam splitter 24. The measurement optical beam 28 passes through a small multipass gas cell 30, providing sufficient path length for suitable sensitivity to produce a modifed measurement beam 28'.

Figure 2:
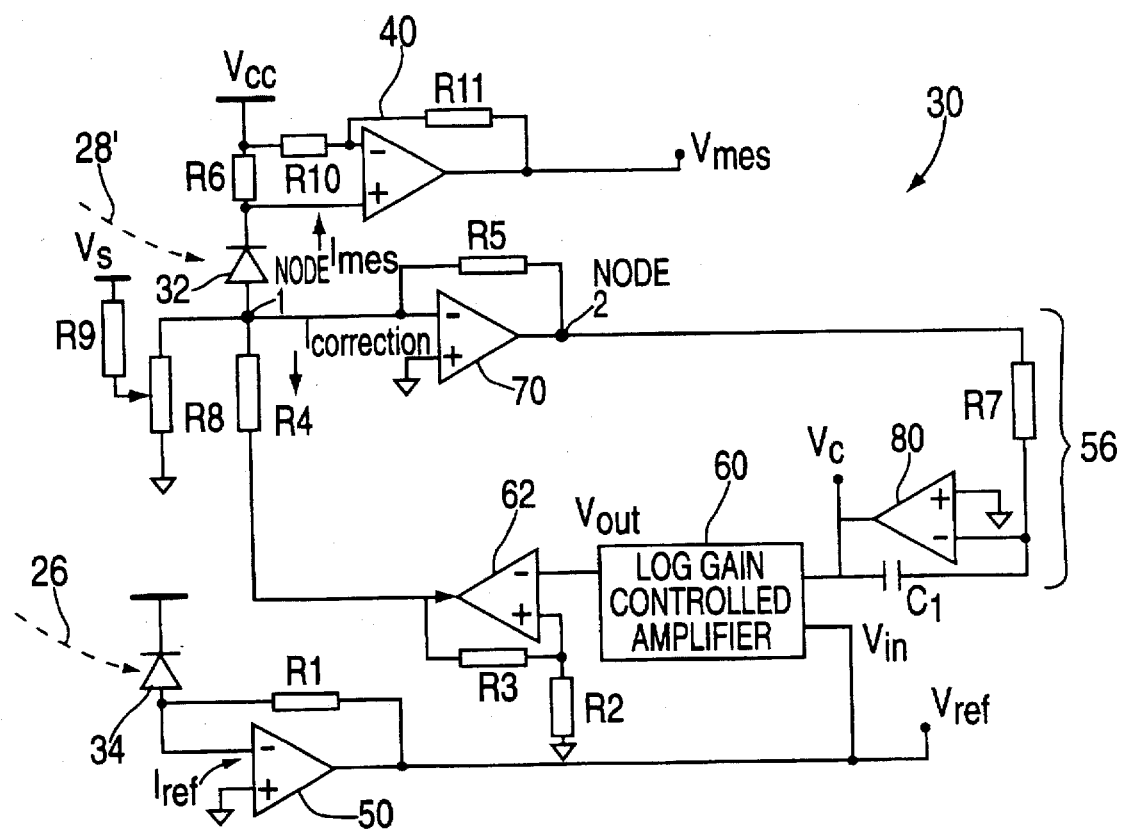
FIG. 2 is a schematic diagram of exemplary circuitry that defines the invention.

Referring also to FIG. 2, measurement beam 28' and reference beam 26 are input into detector 38 and are converted into photocurrents $I_{mes}$ and $I_{ref}$ by photodiodes 32 and 34 respectively. Photocurrents $I_{mes}$ and $I_{ref}$ generate a ratio voltage signal $V_c$ having laser common-mode excessive noise canceled, as described below. $V_c$ is used to determine gas species density which is proportional to partial pressure value.

An alternative sensor construction utilizes a 2×2 single-mode fiber-optic beam splitter. The output of the laser diode is coupled into a small-core single-mode fiber (<10 μm core diameter) by first collimating the beam to pass through an optical isolator, and then focusing the beam into the single-mode fiber. The fiber construction offers flexibility in alignment and in sensor system configurations. By using a n×2 fused coupler, the fiber approach potentially allows multiplexing of several optical wavelengths near 1.5 μm over one optical path in a sensor design.

Recognizing that both configurations using free standing optics or fiber coupled optics may be advantageous for different purposes, the improved detector design and proposed novel self-calibration techniques are applicable to both sensor configurations.

Figure 3A:
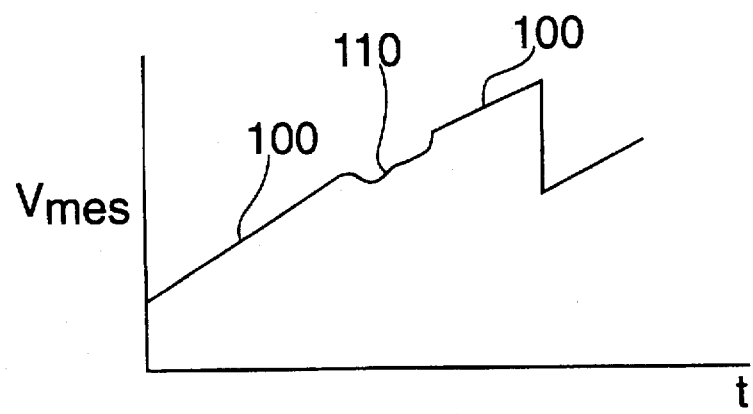
FIGS. 3a–c are voltage waveforms associated with the invention.

Referring to FIG. 2, $I_{mes}$ is input via R6 and R10 to the inverting terminal of op amp 40 characterized as an inverter gain stage amplifier. $V_{mes}$ is the output of op amp 40 and is proportional to $I_{mes}$. FIG. 3a illustrates the waveform of $V_{mes}$ which comprises two components. Component 100 is the linear element proportional to the saw-tooth current ramp input to laser 20 discussed below. Component 110 represents the signal due to the gas absorption.

Figure 3B:
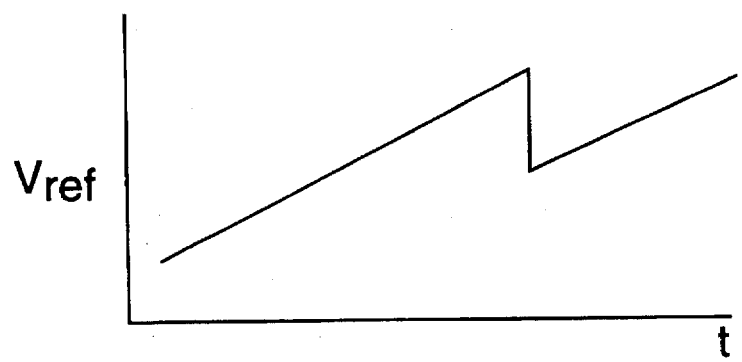

$I_{ref}$ is input to the inverting terminal of op amp 50 characterized as a transimpedance amplifier. $V_{ref}$ is the output of op amp 50 and is proportional to $I_{ref}$. FIG. 3b illustrates the waveform of $V_{ref}$.

$V_{in}$ (equal to $V_{ref}$) inputs into a feedback loop 56 via log-gain controlled amplifier 60 along with control voltage $V_c$. Feed back loop 56 compises amplifier 60, op amp 62, resistor R4, op amp 70 characterized as a trans impedance configuration, an integrator circuit comprising R7, C1 and op amp 80. Amplifier 60 is controlled by the transfer function $$\log (V_{out}/V_{in}) = (1/G) * V_c + F \qquad (1)$$

where G and F are constants given by the temperature-compensated logarithmic amplifier 60 with a typical value of 0.5 and 0.25 respectively. As is obvious to those skilled in the art, $V_{out}$ is proportional to $V_{in}$ with a gain factor which is controlled by the feedback loop where the gain factor can be for example, linear, logarithic or any other function format. $V_{out}$ is input into op amp 62 characterized as a buffer stage. $V_{out}$ forces the voltage at node 2 to zero volts by changing the effective value of $I_{correction}$ which is proportional to $I_{ref}$.

In operation, if $I_{mes} > I_{correction}$ (voltage at node 2≠0), then a current input into op amps 70 and 80 causes $V_c$ to increase and $V_{out}$ to decrease resulting in $I_{correction}$ to increase until voltage at node 2=0. The opposite relationship exists if $I_{mes} < I_{correction}$. Negative current flows from C1, causing $V_c$ to decrease, through op amp 70 to node 1 causing and $V_{out}$ to increase and reduce the value of $I_{correction}$ until node 2=zero volts.

Figure 3C:
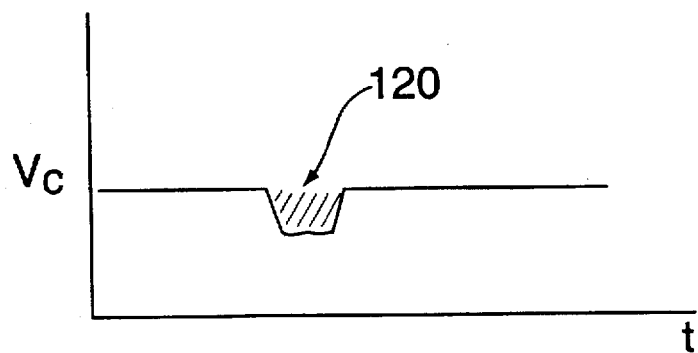

Until feed back loop 56 forces $I_{mes} = I_{correction}$, current (either positive or negative) flows through amplifier 70 resulting in stored voltage (either positive or negative) across C1 that is integrated to arrive at $V_c$. When photocurrent balance is achieved at node 1 for canceling the laser common-mode noises, the feedback loop control voltage $V_c$, as shown in FIG. 3c, relates to measurement and reference photocurrents $I_{mes}$ and $I_{ref}$ by the follow equation:

$$V_c = G \log (I_{mes}/I_{ref}), \qquad (2)$$

where the area 120 represents the signal relating to the volume of gas sensed in chamber 30.

Feed back loop 56 may be tuned to provide a high response time in the μsec. range or higher in response to changing values of $I_{mes}$ or $I_{ref}$. The response time may be varied by adjusting R7 and C1 as is known to those skilled in the art.

In an alternate embodiment, DC components not related to the measurement and reference laser beam-generated signals 28' and 26 respectively, such as amplifier DC offset and photodetector dark currents, can be effectively balanced using the bias resistor pair $R_8$ and $R_9$, connected to a power supply $V_s$ as a DC current sink. These DC components, if not properly removed, may lead to noticeable signal baseline distortion and reduce the effectiveness of common mode noise cancellation. During the calibration stage of detector 38, a bias voltage is added to node 2 by adjusting the value of R8 to force current into or out from node 2 to cause the voltage at node 2 to be zero, thereby, zeroing out the effects of the DC components relating to component operating imperfections. As is readily apparent to those skilled in the art, the bias voltage can be supplied by a microprocessor controlled digital-to-analog converter that allows for continous calibration of the detector circuit 38.

With the embodiment of the invention shown in FIG. 2, the sensor as shown in FIG. 1 is capable of measuring absorption on weak vibrational overtone and combination bands of targeted molecules. The absorption is described by Beer's Law:

$$I_w = I_{o,w} \exp\{-S_T g_w Nl\} \qquad (3)$$

where $I_{o,w}$ is the initial laser intensity at frequency w, $I_w$ is the transmitted intensity after propagation through a path-length $l$, $S_T$ is the temperature dependent transition linestrength, N is the number density of the absorbing molecules, and $g_w$ is the Voigt line-shape function.

Referring again to FIG. 1, the diode laser 20 is thermally stabilized at an operating temperature such that its output wavelength is close to a spectral absorption frequency w of a gas component. The thermal tuning rate of diode lasers is on the order of 0.1 to 0.3 nm/°C, allowing access to multiple absorption lines. A periodic saw-tooth current ramp is applied to the laser diode, where the self-heating of the p-n junction induced by the input driving current produces small temperature changes that lead to similar temperature-induced wavelength tuning. The low-frequency saw-tooth current ramp typically produces a wavelength tuning of 1 to 2 $cm^{-1}$, allowing full resolution of an atomspherically broadened absorption line-shape. $V_{mes}$ and $V_{ref}$ are depicted in FIGS. 3a-b, where the magnitude of the measurement signal attenuation is determined by eq.(3). The logarithmic ratio output $V_c$ shown in FIG. 3c, contains the area 120 under the absorption Voigt lineshape which is proportional to gas sample density.

$V_c$ is input into a digital signal processor 27 where initial system calibration, a relation or a numerical look-up table between the gas molecular density to that of the integrated area under the log-ratio absorption signal in FIG. 3c, is stored in the system memory. The calibration table is established with initial system parameters such as laser driving current ramp and temperatures, optical beam splitting ratio, detector and circuit response values, etc. The sensor is then used to determine a gas components density by comparing the measured integrated absorption signal to the calibration table in the system memory. The partial pressure value can be directly calculated using the measured gas component number density N and gas temperature T via the relation P=NkT, where k is Boltzmann's constant.

After a calibrated sensor is placed in field use for an extended period of time various parameters, such as temperature, humidy and dirt, may lead to the original system calibration table to change, shifting system response characteristics away from that given by the initial calibration table. Readout errors will result due to these unknown changes.

Humidity effects fall into two categories: water vapor in the optical absorption cavity and humidity condensation on optical components. Water vapor in the gas sample cavity does not present problems to the spectral absorption sensing. For example, for $O_2$ sensing, the strong absorption lines are at 760 nm, where nearby water vapor absorption lines are around 820 nm. Likewise, for $CO_2$ sensing at around 1.57 µm wavelength, a group of spectral absorption lines having absorption strength slightly greater than the $O_2$ lines at 760 nm can be readily separated from $H_2O$, CO absorption lines. Therefore, the presence of water vapor does not affect gas component density measurement.

Humidity condensation presents a different set of problems, since it will scatter and attenuate optical signals differently in the signal and reference paths. Without compensation, such signal attenuation will be interpreted as signal absorption, leading to significant errors. The problem is further complicated by the space operation environment, such as spacesuit applications, where wide operating temperature range and high humidity in human breathing air make the condensation more likely to occur. Similarly, since the sensor has an open optical path, dirt may build-up on optical components for long-term applications and cause similar signal attenuation. The dirt may result from, for example, the volatile organic compounds in human breathing air after condensed moisture in a sensor cavity is removed via evaporation.

Figure 4:
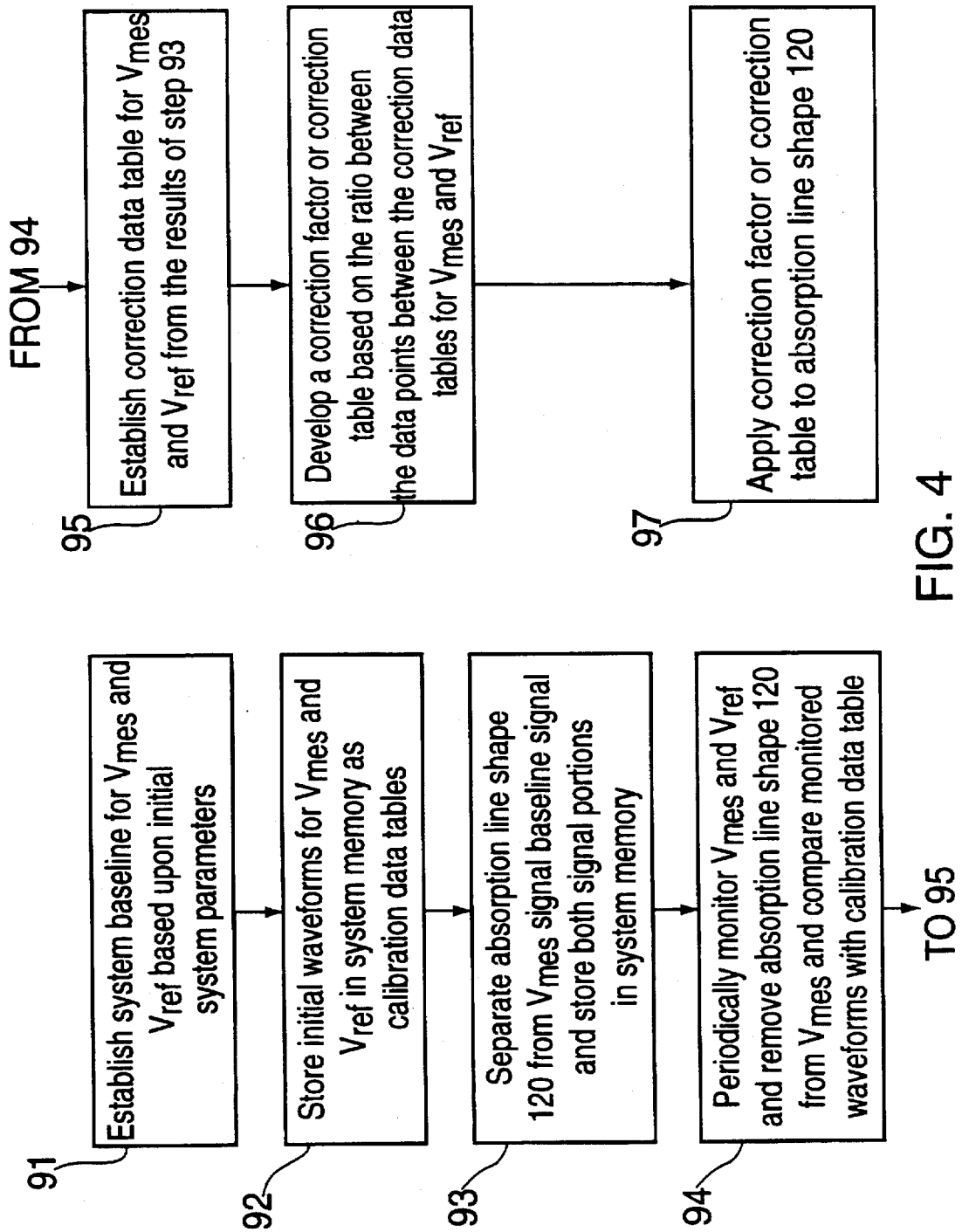
FIG. 4 is a method of providing dynamic scaling to correct for errors due to environmental effects.

A dynamical scaling method corrects for these error factors as shown in FIG. 4. An assumption behind this method is that the gas molecule to be measured will maintain its molecular form. The method consists of establishing a system reference for $V_{mes}$ and $V_{ref}$ based on initial system parameters including diode power output, optical beam splitting ratio, optical path contamination, photodector response, amplifier response, etc. 91; storing an initial waveform for each $V_{mes}$ and $V_{ref}$ in system memory as calibration data tables 92; separating absorption line shape 120 from $V_{mes}$ signal baseline signal and store both signal portions in system memory 93; periodically monitor $V_{mes}$ and $V_{ref}$ and remove absorbtion line shape 120 from $V_{mes}$ and compare signals to calibration data table 94; establishing a correction data table for each $V_{mes}$ and $V_{ref}$ by comparing data in 94 with calibration data table generated in 92 above, 95; developing a correction factor or correction table based on the ratio of correction data for $V_{mes}$ and $V_{ref}$ 96; and applying correction factor or correction table to absorption line shape 120, at step 97. The signals $V_{mes}$ and $V_{ref}$ represent a convoluted system opto-electronic-mechnical response characteristics. The invention is capable of removing signal components not related to input optical signals, as described above. Therefore, by comparing the non-absorption portion of $V_{mes}$ and $V_{ref}$ with their initial calibration values stored in the system memory, self-calibration factors in the form of scaling constants or a time-dependent function within a current ramp for both signals can be established. The ratio of the correction factors is used to correct for the logarithmic lineshape signal to calculate integrated absorption areas. As such, the dynamical scaling-based self-calibration processes periodically and actively measures the signal characteristics, and applies the correction factors such that the system response will match the function established at the initial calibration processes.

It is noted that this self-calibration approach is a generic process applicable to any gas that can be measured with the diode laser spectral absorption technique.

The current ramp induced diode output wavelength scanning shown in FIGS. 3a-c is on the order of <0.1 nm. Therefore, humidity condensation and dirt build-up within the optical path will appear to be spectrally flat within the absorption band of specific gas-component absorption lines. The signal attenuation resulting from such build-up will proportionally reduce $V_{mes}$ and the absorption lineshape while the reference signal will not be affected. Here, only a correction factor for the measurement signal needs to be calculated using the non-absorption portion of the baseline signal. This is actually a simplified case of the self-calibration process. This process can be periodically applied or on demand. Another benefit provided by the dynamical scaling process is that it will provide a measure to determine system degradation such as laser diode output aging or extent of dirt build-up in the optical path.

Test results indicate that common mode excessive noise can be reduced by 50 dB within the operating bandwidth of the integrator feedback loop, which for the most part is less than 100 kHz.

The dependence on temperature of the integrated absorption measurement area 120, can be effectively eliminated by selecting an absorption wavelength with a very low temperature-dependent line-strength. In the case of $O_2$, a number of lines within 760 to 761 nm and 763 to 764 nm, corresponding to the rotational quantum numbers 11, 13, have an absorption line-strength temperature dependence on the order of <0.05%/°C. Fortunately, these lines are among the strongest absorption lines of $O_2$, and are accessible with a number of commercially available FP or DFB laser diodes. A group of $CO_2$ absorption lines around 1.57 μm exhibit similar behavior. These lines have slightly stronger line strength than the 760 nm $O_2$ lines and they are clearly separated from other absorption lines for $H_2O$, CO, and other gas components. By measuring the integrated absorption strength at these spectral locations, temperature-independent gas species number density N can be determined. The partial pressure value can be calculated as p=NkT, where T is the air temperature in the gas cell. In applications for which gas density alone is sufficient to provide the necessary information for monitoring and control purposes, the sensor system will be simplified since no air temperature sensor and associated electronics are required.

Figure 5:
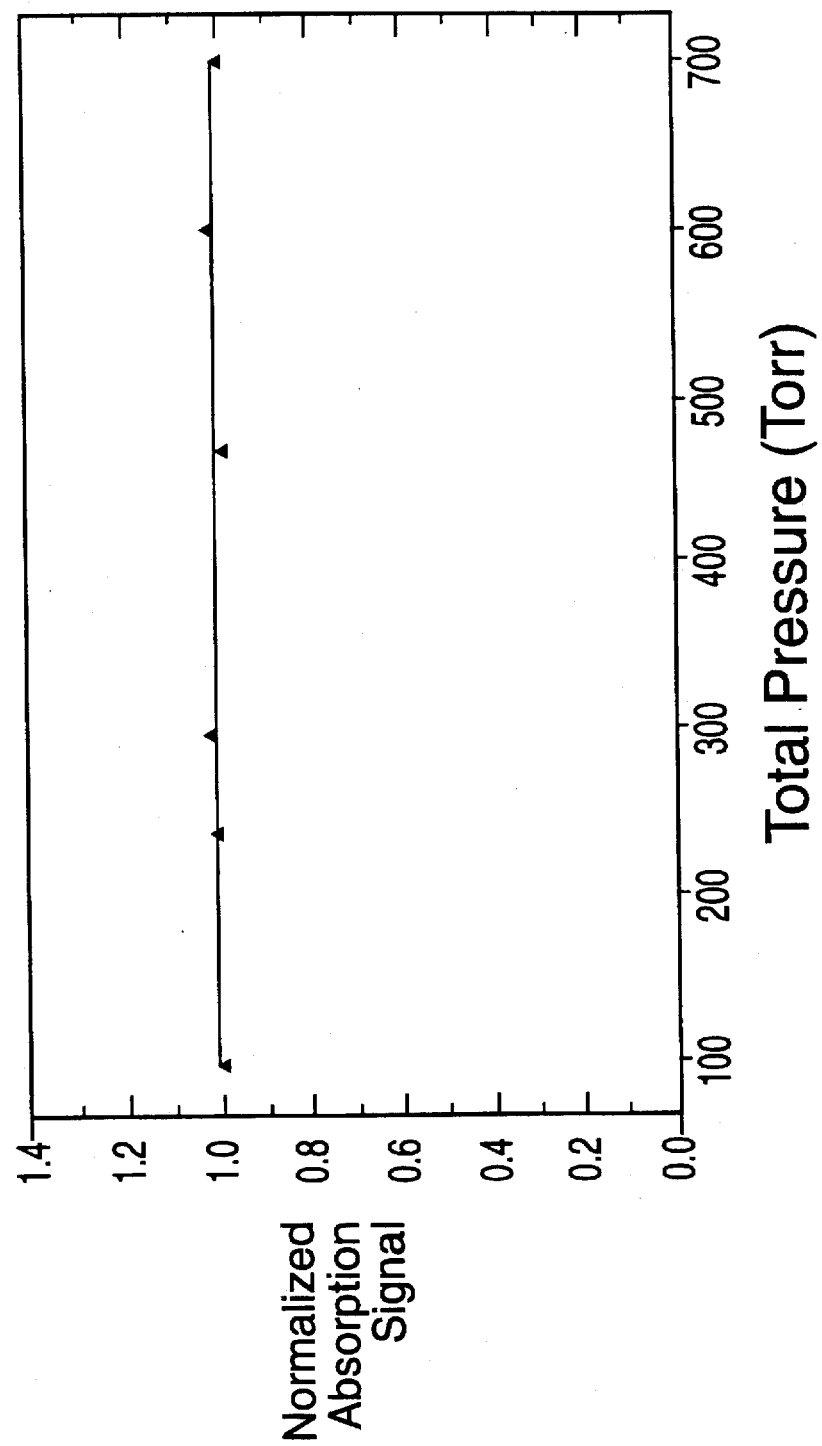
FIG. 5 is a graph of an absorption signal vs. total gas pressure and temperture.

The present diode laser direct absorption approach using detector 38, with the diode modulated at low frequencies (10 to 100 Hz), is capable of resolving a pressure-broadened line-shape. In the case of $O_2$ measurement, the individual spectral lines can be separated at a total pressure of up to 75 psia, as verified by HITRAN data base. Experimental results show that the spectral line-shape half-width increases almost linearly with pressure due to the collision broadening processes; the integrated absorption area 120 stays the same. One set of the data for $O_2$ measurement is shown in FIG. 5. In this experiment, 100 torr pure oxygen at a constant temperature is released into a gas sample cavity. The integrated absorption signal is measured and normalized to 1. Nitrogen gas was then slowly added to the gas cell while maintaining the same temperature. As the total gas pressure increases at a constant temperature, the integrated absorption signal remains constant with accuracies better than 1%, as limited in most part by instrument uncertainties. This demonstrates that the gas density measurement as well as the system calibration is independent of total gas pressure and mixture. Therefore, this sensing approach provides reliable gas component density and partial pressure measurement even as the total pressure and gas mixture changes during applications. This also indicates that when the sensor system is calibrated in one environment, it will be fully functional in other application environments without the need for re-calibration. Additionally, the calibration processes can be significantly simplified as only pure gas samples such as $O_2$ and $CO_2$ are required to perform the initial calibration, regardless of the gas composition in applications. With such a simplified design consideration, a much simplified, portable, field-service calibration module can be readily constructed to periodically calibrate the sensor system. Coupled with the proposed self-calibration processes, it is expected this system design will be able to maintain a high degree of long-term system stability and data accuracy for a wide range of application conditions.

The integrated absorption signal also relates linearly to gas components in a linear fashion as shown in our experiments (better than 1% accuracy) for both $O_2$ and water vapor. This indicates that the sensor calibration look-up table can be easily stored as a linear response function. In addition, during the necessary field services, only one calibration point needs to be established, as we can use the system self-calibration approach to re-build the calibration table while maintaining absolute system accuracy levels.

The following table lists components and typical values which may be used to construct the circuit shown in FIG. 2 for operation at a 100 kHz bandwidth.

TABLE NO. 1

| Component | Designation | Type or Value |
|---|---|---|
| Resistor | R1, R4, F5 | 2.43 KΩ |
| Resistor | R2, R3, R10 | 4.99 KΩ |
| Resistor | R6, R7 | 10 Ω |
| Resistor | R8 | 100 KΩ |
| Resistor | R9 | 50 KΩ |
| Resistor | R11 | 24.3 KΩ |
| Capacitor | C1 | 1500 pf |
| Op Amp | 40, 50, 62, 70, 80 | AD817 |
| Log Gain Controlled Amplifier | 60 | AD603 |
| Photo diodes | 32, 34 | EG&G FFD-100 or FFD-200 |

It will be understood that the particular embodiments described above are only illustrative of the principles of the present invention. The invention has application in any measurement device which detects a small signal in combination with high noise content and further utilizes a reference signal. Such applications may include acoustic, infared, frequency or other types of measurement systems. Various modifications could be made by those skilled in the art without departing from the scope and spirit of the present invention, which is limited only by the claims that follow.

What is claimed is:

1. An electronic signal noise cancellation system comprising:
   a) a source of measurement current representing information signals impressed on a carrier current signal that is modulated by undersirable noise signals;
   b) a source of reference current representing said carrier current signal exclusive of said information signals and modulated by said noise signals;
   c) a voltage source generated as a function of said reference current and a feedback control voltage, said voltage source causing the flow of a correction current modulated by said noise signals;
   d) combining means for additively combining said measurement current and said correction current in a way which substantially cancels the undesirable noise signals from said measurement current and further produces said feedback control voltage which comprises an output signal containing the information component of said measurement current.

2. The signal noise cancellation system of claim 1, further comprising a voltage biasing means for adjusting the voltage level at said combining means to be equal to zero volts in the absence of said measurement and reference currents.

3. An electronic signal noise cancellation system suitable for use with optical sensor systems comprising:
   a) a source of measurement current representing information signals impressed on a carrier current signal that is modulated by undesirable noise signals;
   b) a source of reference current representing said carrier current signal exclusive of said information signals and modulated by said noise signals;
   c) a voltage source generated proportional to said reference current with a gain factor controlled by a feed back voltage, said voltage source causing the flow of a correction current modulated by said noise signals;
   d) combining means for additively combining said measurement current and said correction current in a way which substantially cancels the undesirable nosie signals from said measurement current and further produces said feedback control voltage which comprises an output signal containing the information component of said measurement current.

* * * * *